United States Patent [19]
Nigam

[11] Patent Number: 6,061,592
[45] Date of Patent: May 9, 2000

[54] DEVICE FOR DETECTING TACHYCARDIA USING A COUNTER

[75] Inventor: Indra B. Nigam, Lake Oswego, Oreg.

[73] Assignee: Biotronik Mess-und Therapiegeraete GmbH & Co. Ingenieurbuero Berlin, Berlin, Germany

[21] Appl. No.: 09/073,829

[22] Filed: May 6, 1998

Related U.S. Application Data

[60] Provisional application No. 60/045,848, May 7, 1997.

[51] Int. Cl.⁷ .............................. A61B 5/04; A61B 5/0402
[52] U.S. Cl. ............................................ 600/518; 600/515
[58] Field of Search ..................................... 600/515, 518

[56] References Cited

U.S. PATENT DOCUMENTS

| | | |
|---|---|---|
| 3,952,731 | 4/1976 | Worstencroft . |
| 4,860,749 | 8/1989 | Lehmann . |
| 5,301,677 | 4/1994 | Hsung . |
| 5,327,900 | 7/1994 | Mason et al. . |
| 5,354,315 | 10/1994 | Armstrong . |
| 5,379,776 | 1/1995 | Murphy et al. . |
| 5,542,430 | 8/1996 | Farrugia et al. . |
| 5,545,186 | 8/1996 | Olson et al. . |

FOREIGN PATENT DOCUMENTS

| | | |
|---|---|---|
| 0 094 758 | 11/1983 | European Pat. Off. . |
| 0 302 577 | 2/1989 | European Pat. Off. . |
| 0 469 817 A2 | 2/1992 | European Pat. Off. . |

*Primary Examiner*—William E. Kamm
*Assistant Examiner*—Carl H. Layno
*Attorney, Agent, or Firm*—Venable; George H. Spencer; Catherine M. Voorhees

[57] ABSTRACT

A device for detecting pathological tachycardia, in particular for use with an implantable device for terminating tachycardias, having a classification device, responding to at least one electrical signal derived from the heart, which if the classification criterion is met outputs an output signal indicating pathological tachycardia, having a plurality of classification devices for checking various classification criteria within one heart interval or on the basis of the evaluation of preceding heart intervals; a controllable counter that is connected to the outputs of the classification devices via first logic means; means for incrementing the counter state of the counter by a predetermined counting amount each time, if during a heart interval at least one of the primary classification signals appears; means for keeping the counter state constant or decrementing it by a predetermined counting amount, if no primary classification signal appears within the heart interval; and discriminator means, which output the output signal indicating the occurrence of pathological tachycardia if the counter state of the counter exceeds a predetermined value.

10 Claims, 1 Drawing Sheet

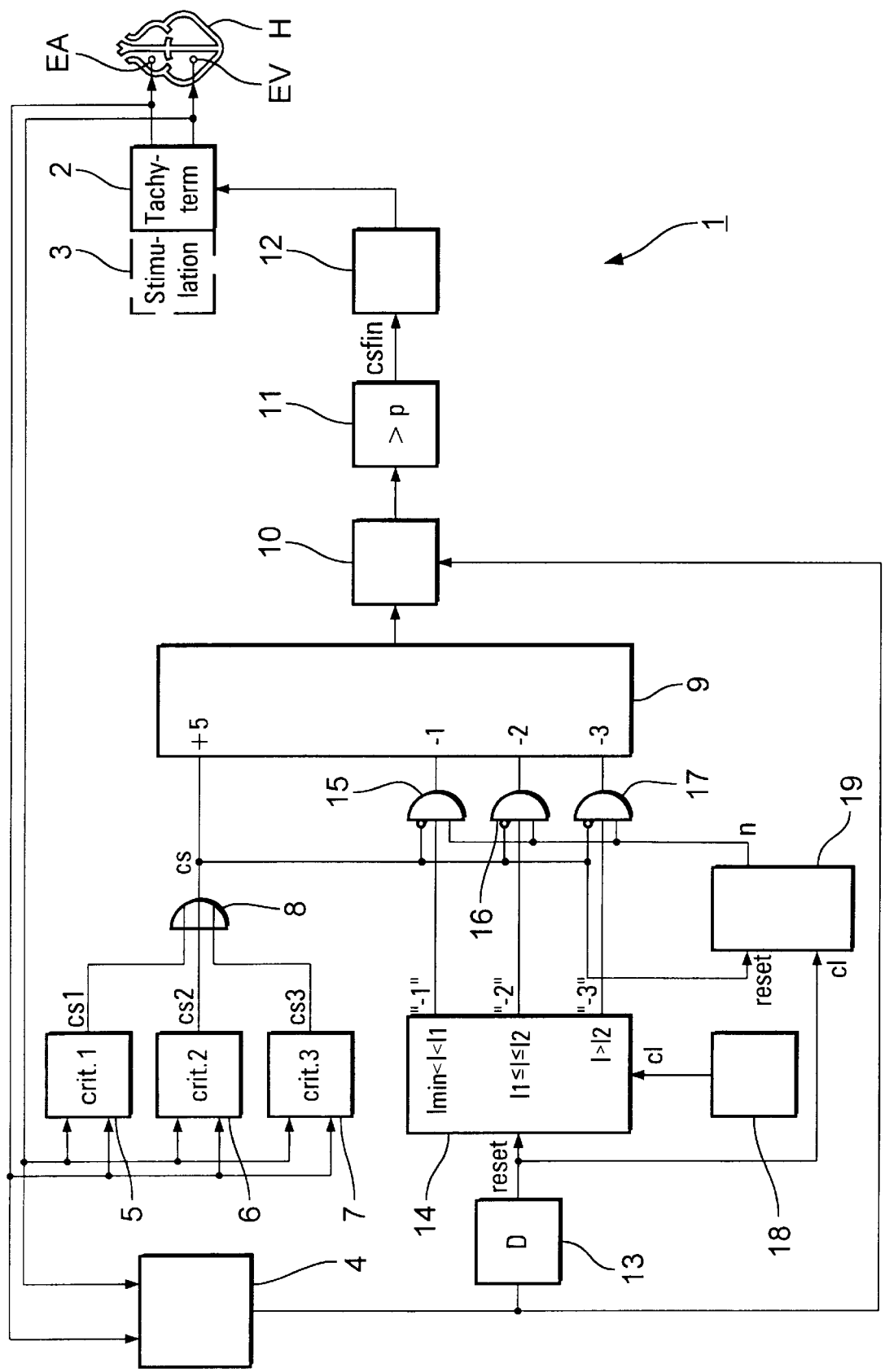

DEVICE FOR DETECTING TACHYCARDIA USING A COUNTER

CROSS-REFERENCE TO RELATED APPLICATION

This application claims the benefit of Provisional Application 60/045,848 filed May 7, 1997.

SPECIFICATION

The invention relates to a device of the generic type defined by the preamble to claim 1.

Such a device can be embodied as a stand-alone diagnostic device, or as a component of an implantable cardiac pacemaker with an anti-tachycardial mode of operation, a defibrillator, cardioverter, or combination device having the function of one of the above devices.

The therapy of tachycardial disturbances in heart rhythm is one of the most important fields in cardiology and is especially a primary field of application of electrostimulation of the heart.

In view of the many ways these problems can be manifested and their many causes, extensive attempts have been made in recent years to improve the preconditions for therapeutic success by means of reliable detection and classification of tachycardial arrhythmias.

In particular, the problem arises of deciding whether a pathological tachycardia is actually present, in contrast to a physiological increase in heart rate. This is especially important, since in the event of an incorrect diagnosis, the wrong therapy, by stimulation, can also cause such pathological tachycardias in the first place.

The most various devices and methods for tachycardia detection are known.

For instance, it is known from European Patent Disclosure EP-A 0 094 758, from the comparison of a current time interval between successive heartbeats with a previously determined mean value on the one hand and with a predetermined (fixed) value on the other, to obtain a criterion for the presence of a pathological tachycardia. Thus some progress was gained, compared with earlier versions, which were based solely on the evaluation of the current heart rate and could not distinguish physiological tachyarrhythmias from pathological ones. For exact classification of the various types of tachycardia, however, the confidence level of this method is insufficient.

Later, various proposals have been made—for instance in European Patent Disclosure EP-A 0 302 577—that the signal form of the EKG (taken conventionally or intracardially) be used as the distinguishing and even predicting criterion. The EKG signal form, however, does not adequately reliably reflect the occurrence of ventricular tachycardia, and the high signal resolution needed to achieve a fair confidence level entails very high expense for measurement and processing.

Quite a number of other approaches make use of analysis of the spatial propagation or correlation of depolarization in the heart tissue. This requires the implantation of many electrodes for signal detection—and for this reason if no other has very little likelihood of realization.

From U.S. Pat. No. 4,860,749, a method for distinguishing a ventricular tachycardia from a sino- or other kind of supraventricular tachycardia is known, in which the atrial and ventricular heart rate (PP interval and RR interval) and the AV interval are measured. If the RR interval is within a predetermined range and is shorter than the PP interval, then the status is readily classified as ventricular tachycardia. If the atrial and ventricular rates are approximately the same as a consequence of 1:1 AV conduction or retrograde conduction, then the measured AV interval is subjected to a comparison with a predetermined value ("sino-AV interval"), and from the result of the comparison the classification criterion is obtained.

In U.S. Pat. No. 5,327,900, a method for discriminating between pathological and physiological tachycardias at comparable atrial and ventricular rates is described, which is based on the associated of the measured AV interval with a predetermined AV time slot that has been determined from the AV interval during normal sinus rhythm.

Another method, in which a great number of additional criteria (on the RR interval and on the ratio between the PP and RR intervals) is employed to ascertain the treatability of an ascertained tachyarrhythmia in the event of virtual agreement between the atrial and ventricular rates, is described in U.S. Pat. No. 5,379,776.

The object of the invention is to disclose a relatively simply designed, implantable, energy-saving device which indicates a pathological tachycardia with great certainty and speed.

This object is attained by a device having the characteristics of claim 1.

The invention includes the concept of creating a device for detecting a pathological tachycardia, particularly for use with an implantable device for terminating tachycardias, in which the detection is made on the basis of a plurality of criteria to be examined simultaneously within one heart interval. The term "simultaneous" detection is intended to mean that these criteria are employed jointly within one detection cycle. Naturally, with processing technology, this can also occur in rapid chronological succession. The only significant factor here is that the results be available together without delay, and can be correlated cohesively on a beat-to-beat basis.

To this end, in particular, a counter and means are provided for differentially varying the counter state as a function of the outcomes of the examination of the individual criteria. In principle, the counter state is increased by a predetermined counting amount each time at least one of the primary classification signals that indicate the presence of a criterion has occurred within one heart interval. In addition, output means are provided for outputting a signal characterizing the occurrence of tachycardia, whenever a predetermined counter state has been exceeded.

In an advantageous further feature, means for maintaining or decreasing the counter state are also provided, if none of the criteria that are definitive for the occurrence of tachycardia are met during the heart interval. In particular, the counter is decremented only whenever at least two heart intervals, within which none of the criteria for the presence of tachycardia have been met, succeed one another.

Advantageously, the counting amount by which the counter is incremented if one or more of the criteria are met is also greater in each case than the counting amount by which the counter is decremented if they are not met.

In another advantageous further feature, the counting amount by which the counter is decremented is selected such that in each case it decreases by the spacing between two heartbeats. For ascertaining a current counting amount by which the counter is decremented, an auxiliary counter is provided in particular, which is started at the beginning of a heart interval and stopped at the end thereof; whatever counter state is reached then forms a measure of the counting amount by which the counter state is reduced.

Finally, in a preferred embodiment, the counter is set to zero whenever no elevated heart rate is found for a predetermined number of successive heart beats.

Advantageous further features of the invention are also defined by the dependent claims and described in further detail below, together with the description of the preferred embodiment of the invention, in conjunction with the drawing.

BRIEF DESCRIPTION OF THE DRAWING

The sole FIGURE of the drawing is a function block circuit diagram of a device in a preferred embodiment of the invention.

DETAILED DESCRIPTION OF THE INVENTION

In the drawing, the layout of a device 1 for tachycardia detection and classification, connected to the heart H via one atrial electrode and one ventricular electrode EA and EV, respectively, is shown in terms of its essential function elements in conjunction with the invention.

The device 1 is connected to a tachycardia detection unit 2 that is designed to be implantable together with the tachycardia detection device 1. It includes a stimulator device, shown in dashed lines as a block 3, which by way of example forms the generator part for a combined implantable defibrillator and cardiac stimulation device. Such combinations are known in principle and are intended here merely as one example for the manifold versatility of the device of the invention.

The other component groups form a detection and evaluation unit for electrical signals, picked up from the heart, that is are used to detect tachycardia and, if tachycardia is reliably detected, to initiate stimulation for tachycardia termination via the component group, the initiation being done by outputting a control signal. This is also understood to mean its use for defibrillation.

Via the electrodes EA, EV, the signals from the heart 1 are passed on via amplification and signal forming means (not shown), which are known per se, to a heartbeat detector 4, which controls the detection cycles in synchronization with the heartbeat behavior (the heart intervals). In the simple exemplary embodiment shown here, P and R waves are detected via the heart beat detector 4; in the presence of natural or stimulated heartbeats, these waves provide information on the heart rate and thus also allow recognition of physiologically dictated increases in the heart frequency.

The heartbeat detector not only controls the detection cycles but at the same time also serves to detect tachycardial tendencies on the basis of the heart rate (the PP or RR intervals).

It is known that a severely elevated heart rate (tachycardia) can be physiological in nature. The use of tachycardia criteria that serve to distinguish between physiological and pathological tachycardia is therefore contemplated as well.

To this end, the signals derived from the heart H via the electrode $E_A$ and $E_V$ are delivered in parallel to three classification units 5–7, which check for the presence of one of three predetermined criteria crit1–crit3 for pathological tachycardia, which are largely independent of the current rate value, and thus detect the occurrence of tachycardia. Each classification group 5–7 outputs one primary classification signal cs1–cs3. The primary classification signals are then delivered to an OR gate 8.

These tachycardia criteria to be used may be taken in part from the prior art but also individually from a parallel patent application of the present Applicant filed on the same date.

One of these criteria is for instance the speed of changes in the ventricular heart rate (the RR interval) in comparison with a preceding heart interval. In a corresponding version, the question is asked in the first classification unit 5 for instance whether the tachyarrhythmia was of sudden onset. To that end, the currently ascertained mean value for the RR interval (see hereinafter) is subjected to a comparison with a previous mean value. The output signal output by the unit 5 then expresses whether a shortening of the RR interval that exceeds the differential amount stored in memory has occurred, which is assessed as evidence of a sudden onset of the tachyarrhythmia. This is an indication for the presence of a ventricular (pathological) tachycardia or fibrillation.

Another criterion is the ratio of the length of the RR intervals (mean values) to the length of the PP intervals (mean values). If the RR intervals are shorter than the PP intervals, this argues for the presence of ventricular tachycardia. Accordingly, the second classification unit 6, for instance, will have means for determining the PP interval —preferably a mean value of it over a plurality of detection cycles—as well as means for forming a quotient of the RR and PP interval values or mean values, and a following discriminator stage.

Another classification criterion is the stability of the RR intervals over time. Accordingly, in the classification unit 7, for instance, the RR interval values are subjected to a comparison with a programmed stability criterion. (In practice, it is preferred that the differences between the current RR interval mean value and each of the three preceding RR interval mean values be compared with the stability criterion, and stability is assumed to exist if this criterion is met in all three comparisons.) If they are stable, then the question is also asked whether the RR interval mean value is an integral multiple of the PP interval mean value (which is available in unit 6). If it is found that the RR interval mean value is an integral multiple of the PP interval mean value, then what is occurring is an n:1 atrial tachycardia that is transferred to the ventricle. Conversely, if it is found that it is not an integral multiple ("NO" in step S8), this argues for ventricular tachycardia.

Other criteria that can be employed are the regularity of the PR intervals and/or the stability of the PP intervals, or the monotony of the change in the PR intervals over time. These criteria can be employed in additional classification units, or instead of one of the above-specified criteria in units 5–7.

At this point it should be noted that the illustration of the classification units in terms of hardware is merely for purposes of explanation. It will be appreciated that software algorithms, which also accomplish the use of the tachycardia criteria, can also be used.

The output signal cs of the OR gate 8 is delivered to an incrementing input "+5" of a counter 9, which is incremented by a predetermined amount if the tachycardia criteria are met. This value is shown here as five. Other incrementation values may also be used; what is important is that weighting of the events influencing the counter 9 is brought about by the selection of the incrementation value.

Via a gate circuit 10 on the output side of the counter 9, upon detection of a subsequent heartbeat (as a conclusion of the detection cycle), the counter state of the counter 9, on the basis of the heartbeat detector 4 via an activation input of the gate circuit 10, is supplied to a discriminator stage 11. This stage outputs an output signal csfin, if the state of the counter 9 exceeds a predetermined value p. Next, by means of the control signal output stage 12, a stimulation pattern is tripped, which is output by the tachycardia termination unit and is intended to bring about a tachycardia termination. If the counter state of the counter 9 is below p, then the discriminator stage 11 does not output any output signal, and no stimulation for terminating the tachycardia is done.

If via the classification units 5–7 a state that does not meet any of the criteria crit1–crit3, the counter 9 is decremented, under fixed preconditions and in a predetermined way.

To determine the amount of decrementation, the current heart rate is determined and classified in the units 13, 14 and 18 (which are described in further detail hereinafter). Depending on whether the heart rate falls within a bradycardial range, a normal range, or a tachycardial range, the counter is decremented by various amounts.

In the present example, three different decrementation values, "–1", "–3", and "–2", are used, depending on whether the current rate value f is above a first rate threshold value f1, below a second rate threshold value f2, or between the values f1 and f2. (Naturally, still other configurations of values may be employed, including the possibility of maintaining the counter state that has been reached.)

In this way it is attained that the readiness of the device to intervene in tachycardia termination again remains elevated if the heart rate is elevated, or in other words if the heartbeats fall within a tachycardial range. If the heartbeat rate is bradycardial, then this readiness is relatively rapidly diminished by decrementing the counter 9 with the highest decrementing amounts, and there must first be a number of detection cycles within which one of the stages 5–7 has responded, in order to trip a tachycardia termination again. In this way, the system in its reaction readiness adapts to the heart behavior on the basis of past events, so that it does not initiate a tachycardia termination until many indications of a need to do so are in fact present.

To accomplish this function, via an interval counter and discriminator 14, which is triggered by a timer 18 and is reset—delayed via the D element 13—after each heartbeat detected via the unit 4, the length 1, expressed by a counting value, of the most recent heartbeat interval is associated with one of the predetermined ranges "1>12" (corresponding to the heart rate f>f1), "11≦1≦12" (corresponding to f2≦f≦f1), or "1>12" (corresponding to f<f2). At whichever of the three outputs is activated, a decrementation signal corresponding to the applicable association is output, that is, either "–1", "–2" or "–3".

Once the interval counter and discriminator is reset by a signal of the heartbeat detector 4, then no output signal is emitted before a minimal counter state is reached. The counter is thereupon neither decremented nor incremented, on the precondition that none of the circuits 5–7 has responded.

The outputs of the interval counter and discriminator 14 are each connected to a control input of the counter 9, via a respective AND gate 15, 16 and 17. Unblocking of the AND gates 15–17, or in other words switching the decrementation signal, furnished by the interval counter and discriminator 14, through to the corresponding input of the counter 9, is done under the following preconditions:

(a) There is currently no signal present at the output of the OR gate 8 that meets the criteria crit1–crit3, and so the inverting inputs of the AND gates are not activated.

(b) None of the classification units 5–7 has responded during n previous measurement cycles.

The meeting of precondition (b) is documented by a further counter 19, which is clocked via the heartbeat detector 4 and the D element 13 and is reset in each case by an output signal of the OR gate 8. The AND gates 15–17 are unblocked, once the counter 19 has reached a predetermined counter state n. Since the counter is triggered by the output of the D element 13 at the end of each detection cycle, then for this to happen there must have been n detection cycles that elapsed without any response by one of the detection units 5–7.

The invention is not limited in its embodiment to the preferred exemplary embodiments described above. On the contrary, a number of variants is conceivable which make use of the present teaching even in a different kind of embodiment.

In particular, the teaching can be put to use in either hardware or software form, or with a combination of the two.

The procedure sketched out above and the arrangement shown may be modified in manifold ways, for instance by dispensing with the counter 19 and the execution of a decrementation of the counter 9 on a beat-to-beat basis (without assessing whether tachycardia criteria have been met in previous detection cycles).

Of particular interest is also a linkage of the classification units which is modified compared with the above description and in which there are at least some AND linkages, so that a valid classification signal for a pathological tachycardia is output only if the thus linked (provisional) criteria are met all at once.

The device may be an independent unit or may be used in combination with other (especially implantable) appliances, in particular a cardiac pacemaker or a combination pacemaker/defibrillator appliance.

I claim:

1. A device (1) for detecting pathological tachycardia, in particular for use with an implantable device (2) for terminating tachycardias, having a classification device, responding to at least one electrical signal derived from the heart and processing at least one classification criterion, which if the classification criterion is met outputs an output signal (csfin) indicating pathological tachycardia, characterized by a plurality of classification devices (5–7) for checking various classification criteria (crit1-crit3) within one heart interval or on the basis of the evaluation of preceding heart intervals, which each, if one of the classification criteria is met, output one of a plurality of primary classification signals (cs1–cs3);

a controllable counter (9) that is connected to the outputs of the classification devices via first logic means (8);

means (8) for incrementing the counter state of the counter by a predetermined counting amount ("+5") each time, if during a heart interval at least one of the primary classification signals appears;

means for keeping the counter state constant or decrementing it by a predetermined counting amount ("–1", "–2", "–3"), if no primary classification signal appears within the heart interval; and discriminator means (11), which output the output signal (csfin) indicating the occurrence of pathological tachycardia if the counter state of the counter (9) exceeds a predetermined value (p).

2. The device of claim 1, characterized in that the counting amount by which the counter (9) is incremented in the event that a primary classification signal (c11-c13) appears is greater than the counting amount, or each counting amount, by which the counter is decremented if no primary classification signal appears within the heart interval.

3. The device of claim 1, characterized in that the first logic means have an OR gate (8), with whose inputs the outputs of all the classification devices (5–7) are connected at least indirectly.

4. The device of claim 1, characterized in that the first logic means have an AND gate, with whose inputs the outputs of at least some of the classification devices are connected.

5. The device of claim 1, characterized in that the counting amount by which the counter (9) is decremented increases as the spacing between two successive heartbeats increases.

6. The device of claim 5, characterized in that for ascertaining the counting amount by which the counter (9) is decremented, a first auxiliary counter is provided, which is started at the onset of each heart cycle, and whose counter state reached at the end of the heart cycle determines the counting amount by which the counter is decremented.

7. The device of claim 6 characterized in that between the output of the first auxiliary counter (14) and the associated control input of the counter (9), two logic means are connected, which in turn are connected via a control input to the output of the first logic means (8).

8. The device of claim 1, characterized in that the counter is decremented only whenever a predetermined plurality of heart intervals within which no primary classification signal has appeared have succeeded one another.

9. The device of claim 8, characterized by a second auxiliary counter (19), controlled via the classification devices (6–7), for determining the number of successive heart intervals within which no primary classification signal has appeared.

10. The device of claim 8, characterized in that the counter (9) is set to zero if previously at least two heart intervals have succeeded one another within which none of the first output signals has appeared.

* * * * *